United States Patent [19]
Thetford et al.

[11] Patent Number: 6,133,366
[45] Date of Patent: Oct. 17, 2000

[54] COMPOUND, PREPARATION AND USE

[75] Inventors: Dean Thetford, Rochdale; Mark Holbrook, Bury, both of United Kingdom

[73] Assignee: Zeneca Limited, London, United Kingdom

[21] Appl. No.: 09/077,774

[22] PCT Filed: Oct. 18, 1996

[86] PCT No.: PCT/GB96/02545

§ 371 Date: Jun. 1, 1998

§ 102(e) Date: Jun. 1, 1998

[87] PCT Pub. No.: WO97/19948

PCT Pub. Date: Jun. 5, 1997

[30] Foreign Application Priority Data

Nov. 30, 1995 [GB] United Kingdom .................. 9524475

[51] Int. Cl.$^7$ ............................. C08L 67/04; C08L 71/02; C08L 43/02; C09D 11/02; C09D 11/16

[52] U.S. Cl. ......................... 524/505; 524/845; 525/408; 523/160; 523/161

[58] Field of Search ..................................... 524/505, 845; 525/408, 409; 523/160, 161; 106/31.6

[56] References Cited

U.S. PATENT DOCUMENTS

| | | | |
|---|---|---|---|
| 3,312,753 | 4/1967 | Bailey, Jr. et al. | 528/357 |
| 4,500,686 | 2/1985 | Kobayashi et al. | 525/408 |
| 4,704,165 | 11/1987 | Nakamura et al. | 106/413 |
| 5,151,218 | 9/1992 | Haubennestel et al. | 516/77 |
| 5,320,673 | 6/1994 | Carpenter | 106/404 |
| 5,929,177 | 7/1999 | Kataoka et al. | 525/408 |

FOREIGN PATENT DOCUMENTS

| | | |
|---|---|---|
| 569 907 | 11/1993 | European Pat. Off. |
| 39 30 687 | 4/1991 | Germany. |
| 95 34593 | 12/1995 | WIPO. |

OTHER PUBLICATIONS

Morrison, Robert Thornton and Boyd, Robert Neilson; Organic Chemistry 5thEd., Allyn and Bacon, Inc, Boston (p. 874), 1987.

*Primary Examiner*—Vasu Jagannathan
*Assistant Examiner*—Callie E. Shosho
*Attorney, Agent, or Firm*—Pillsbury Madison & Sutro LLP

[57] ABSTRACT

A dispersant which is a phosphate ester of a block copolymer of formula $MeO(C_2H_4O)_m(PES)_n$—H wherein PES is derived from ε-caprolactone, m is 5–60, n is 2–30 and the MW of $MeO(C_2H_4O)_m$ is greater than the MW of $(PES)_n$ and use in aqueous-based paints and printing inks.

10 Claims, No Drawings

COMPOUND, PREPARATION AND USE

The present invention relates to a compound for dispersing particulate solids in an aqueous medium, its method of preparation and compositions containing said compound and a particulate solid, including paints and inks.

Mill-bases for water-borne paints are conventionally prepared by subjecting an aqueous medium containing a water-insoluble particulate solid such as a pigment to a grinding operation in the presence of both a resin and a dispersing agent in order to uniformly distribute the finely divided solid throughout the medium. However, when such mill-bases are added to a paint, the dispersing agent can adversely effect the film-forming characteristics of the paint and/or it durability as a paint film. Some dispersing agents also adversely affect the gloss of the resulting paint film. Consequently, improved dispersing agents are required which are capable of dispersing greater amounts of particulate solid in the medium, and exhibiting increased stability of the dispersion and superior properties in the resulting paint film, especially higher gloss finish.

Canadian Patent Application No 2,022,957 discloses dispersants which are phosphate esters of block copolymers which contain both poly(alkyleneoxy) and polyester chain segments and specifically a phosphate ester of a block copolymer which is polyethyieneglycolmonomethyl ether of MW 750 polymerised with valerolactone which also gives rise to a polyester of MW 750. It has now been found that phosphate esters of block copolymers of this type exhibit superior properties as dispersants for aqueous millbases if the MW of the polyethyleneglycol chain segment is greater than the MW of the polyester chain segment.

According to the present invention there is provided a dispersant which is a phosphate ester of a block copolymer of formula 1

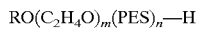   1 wherein

R is $C_{1-4}$-alkyl;

PES is a polyester derived from a cyclic lactone;

m is from 5 to 60;

n is from 2 to 30; and where the molecular weight of $RO(C_2H_4O)_m$ is greater than the molecular weight of $(PES)_n$.

R may be linear or branched but is preferably linear and is especially methyl.

The cyclic lactone is preferably valerolactone and especially ε-caprolactone. When PES represents a polyester derived from valerolactone, the repeat unit is of formula —O—$(CH_2)_4$CO— or —O—$CH(CH_3)$—$(CH_2)_2$CO— and when PES represents a polyester derived from ε-caprolactone, the repeat unit is of formula —O—$(CH_2)_5$CO—.

Preferably m is not greater than 40 and especially not greater than 25.

It is also preferred that n is not greater than 20 and especially not greater than 10.

Preferably the ratio of m:n is not less than 3:1, more preferably not less than 4:1 and especially not less than 6:1.

The MW of the block copolymer of formula 1 is preferably less than 5,000, more preferably less than 4,000, even more preferably less than 3,500 and especially less than 3,000.

The phosphate ester is obtainable by reacting the monoalkyl ether of formula 1 with a phosphating agent wherein the ratio of monoalkyl ether to each phosphorus atom of the phosphating agent is from 3:1 to 1:1 and especially from 2:1 to 1:1.

It is especially preferred that the ratio of monoalkyl ether to each phosphorus atom of the phosphating agent is less than 2, for example, about 1.5:1 when the dispersant is a mixture of mono- and di-phosphate esters.

The phosphate ester may be in the form of a free acid or it may form a salt with an alkali metal, ammonia, an amine, alkanolamine or a quaternary ammonium cation.

The phosphate ester may also be further reacted with an alkanol or alkanolamine. Preferred alkanols are $C_{1-6}$- and especially $C_{1-4}$-alkanols. When the phosphate ester is further reacted with the alkanol additional ester groups are formed and the ratio of the monoalkyl ether of formula 1 to the phosphorus atom of the phosphating agent is less than 2 and especially less than 1.5.

When the phosphate ester is reacted with an alkanolamine, the alkanolamine may form ester and/or amido groups and/or amine salts. It is believed that the reaction product is mainly an amine salt.

Preferred phosphating agents are $POCl_3$, polyphosphoric acid and especially $P_2O_5$.

Preferably, the alkali metal is lithium, potassium and especially sodium.

Examples of alkanolamines are ethanolamine, diethanolamine, 2-dimethylamino ethanol and 2-amino-2-methyl-1-propanol.

The block copolymer of formula 1 may be made by any method known to the art and is preferably made by reacting a polyethyleneglycol monoalkylether of formula 2 with a cyclic lactone such as valerolactone or ε-caprolactone

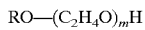   2 wherein R and m are as denied hereinbefore.

The reaction is preferably carried out in an inert atmosphere such as nitrogen under anhydrous conditions and is also preferably catalysed by a metal salt which is soluble in the reaction mass. A preferred catalyst is a titanium salt, particularly an alkoxide such as titanium tetra n-butylate. The reaction is preferably carried out at temperatures above 100° C. and preferably above 150°C. In order to avoid charring of the copolymer the temperature is preferably less than 220° C. and especially less than 200°C.

The reaction between the monoalkyl ether of formula 1 and the phosphating agent is also preferably carried out in an inert atmosphere such as nitrogen under anhydrous conditions. The reaction may be carried out in an inert solvent but is more convenient to react the monoalkyl ether with the phosphating agent in the absence of a solvent. The reaction temperature is preferably above 60 and especially above 80° C. In order to avoid charring of the dispersant, the temperature is preferably less than 120 and especially less than 100° C.

It is particularly preferred that the block copolymer is not isolated but is directly converted to the phosphate ester by reaction with a phosphating agent. The preferred phosphating agent in this one-pot synthesis is polyphosphoric acid.

When the dispersant contains additional ester, amide and/or amine salt groups formed by reacting the phosphate ester with an alkanol or alkanolamine the alkanol or alkanolamine may be reacted with the phosphate ester under the same conditions as are used for reacting the monoalkyl ether with the phosphating agent.

As noted hereinbefore the dispersants according to the present invention are suitable for uniformly distributing a particulate solid in a liquid medium, especially an aqueous medium.

Thus, according to a further aspect of the invention there is provided a composition comprising a dispersant as defined hereinbefore and a particulate solid.

Preferably, the composition further comprises a liquid, especially one in which the dispersant is at least partially soluble and more especially is either water or an organic liquid which is miscible with water including mixtures thereof. Examples of suitable liquids include alcohols such as $C_{1-10}$-aliphatic alcohols; glycols such as $C_{2-6}$-alkylene glycols; alcohol ethers such as methoxy-, ethoxy-, propoxy- and butoxyethanol and methoxy-, ethoxy- and propoxypropanol; and glycol ethers such as diethylene glycol and propylene glycol. Generally, the liquid is selected to meet the requirements of the end-use to which the composition is put, especially compatibility with any medium with which it is to be diluted. Preferably, the liquid comprises at least 25%, more preferably at least 50% and especially at least 75% by weight water relative to the total weight of the composition.

The composition may comprise an intimate mixture of the dispersant and the particulate solid but preferably comprises a coating of the dispersant on a finely divided particulate solid. Preferably the particulate solid has a mean diameter of less than 15 $\mu$, more preferably less than 10 $\mu$, especially less than 5 $\mu$ and most especially less than 3$\mu$.

The particulate solid can be any material which it is desired to stabilise in a finely divided state in a liquid medium. Examples of suitable solids are pigments and fillers for inks, paints and other surface coatings; magnetic metals or alloys and magnetic oxides, for use in the production of magnetic tapes, discs and memory devices; dirt and soil particles; biocides, agrochemicals and pharmaceuticals. The composition, whether dry or in the form of a dispersion in a liquid medium, may contain other ingredients such as resins, binders, fluidising agents, anti-sedimentation agents, plasticisers, humectants, coalescents, co-solvents, thickeners and preservatives. These ingredients may be soluble in, partially soluble in, insoluble in, or dispersed in the liquid medium.

If the solid is a pigment, it is preferably an inorganic pigment, a metallic pigment, or a metal salt of an organic dyestuff (sometimes referred to as a lake or toner). It may come from any of the recognised classes of pigments described, for example, in the Third Edition of the Colours Index (1971) and subsequent revisions and supplements thereto, under the chapter headed "Pigments".

Examples of inorganic pigments are titanium dioxide (including Anatase and Rutile forms, and high UV absorbing ultra-fine titanium dioxide), zinc oxide, Prussian Blue, cadmium sulphide, iron oxides (including transparent iron oxides), ultramarine, mica (including pearlescent pigments made by surface treating mica with, for example, fine titanium dioxide) and the chrome pigments, including chromates, molybdates, and mixed chromates and sulphates of lead, zinc, barium, calcium and mixtures and modifications thereof which are commercially available as greenish-yellow to red pigments under the names of primrose, lemon, middle, orange, scarlet and red chromes.

Examples of metallic pigments are aluminium flake, copper powder and copper flake.

Examples of metal salts of organic dyestuffs are the azo metal salt pigments such as Cl Pigment Red 48 (also known as 2B Toner or Permanent Red 2B), Cl Pigment Red 53 (also known as Lake Red C or Red Lake C), Cl Pigment Red 52, Cl Pigment Red 57 (also known as 4B Toner, Lithol Rubine, Rubine Toner or Permanent Red 4B), Cl Pigment Red 58, Cl Pigment Red 247, Cl Pigment Yellow 61, Cl Pigment Yellow 62, Cl Pigment Yellow 183 and Cl Pigment Yellow 191.

Examples of fillers are calcium carbonate, hydrated alumina, talc, quartz, silica (precipitated, pyrogenic and synthetic), metal silicates, barium and calcium sulphate, china clay, antimony oxide, powdered slate, wollastonite and chopped glass fibre.

The composition may be made by any method known to the art. Thus, it may be prepared by mixing together the dispersant and particulate solid and preferably then grinding the composition to obtain the desired particle size of the solid. Preferably, however, the dispersant may be added to the particulate solid in the presence of a liquid during the final preparation or finishing stages of the particulate solid. Generally, the composition is, however, prepared by mixing the dispersant, particulate solid and a liquid medium and then grinding or milling the composition to obtain the desired particle size of the particulate solid. The liquid medium may be water or an organic liquid in which the dispersant is preferably at least partially soluble. If the composition is required in dry form, the liquid medium is preferably volatile so that it may be readily removed from the particulate solid by simple separation means such as evaporation. It is preferred however that the composition comprises the liquid medium.

If the dry composition consists essentially of the dispersant and the particulate solid, it preferably contains at least 0.2%, more preferably at least 0.5% and especially at least 1% by weight of dispersant based on the weight of the particulate solid. Preferably, the dry composition contains not greater than 100%, preferably not greater than 50%, more preferably not greater than 20% and especially not greater than 10% by weight dispersant based on the weight of the particulate solid.

When the composition comprises a dispersant, particulate solid and a liquid medium, it preferably contains at least 5%, more preferably at least 20%, especially at least 40% and most especially at least 50% particulate solid based on the total weight of the composition. Preferably, the composition contains not greater than 90%, more preferably not greater than 80% and especially not greater than 75% by weight solid based on the total weight of the composition. The preferred amount of dispersant relative to the particulate solid is as defined hereinbefore for the dry composition.

As stated hereinbefore, the dispersants of the invention are particularly suitable for preparing aqueous mill-bases where the particulate solid is milled in a liquid in the presence of both the dispersant and a film-forming resin binder.

Thus, according to a still further aspect of the invention there is provided an aqueous mill-base comprising a particulate solid, dispersant and a film forming resin.

Typically, the mill-base contains from 20 to 70% by weight particulate solid based on the total weight of mill-base. Preferably, the particulate solid is not less than 30 and especially not less than 50% by weight of the mill-base.

The amount of resin in the mill-base can vary over wide limits but is preferably not less than 10%, and especially not less than 20% by weight of the continuous phase/liquid phase of the mill-base. Preferably, the amount of resin is not greater than 50% and especially not greater than 40% by weight of the continuous phase/liquid phase of the mill-base.

The amount of dispersant in the mill-base is dependent on the amount of the particulate solid but is preferably from 0.5 to 5% by weight of the mill-base.

The resin may be any film-forming resin which is capable of acting as a binder in aqueous-based paints and printing inks. The resin is preferably capable of undergoing a cross-linking action with a cross-linker and is preferably an acrylic or acrylate polymer containing ethylenically unsaturated groups.

The invention is further illustrated by the following examples in which all parts and percentages refer to amounts by weight unless indicated to the contrary.

Intermediate Block Copolymers

In the following Intermediate block copolymers polyethyleneglycol monomethyl ether is referred to as MeOPEG and the polymer derived from ε-caprolactone is referred to as "cap". The figures in parentheses refer to the approximate molecular weight of the polymer repeat units.

Intermediate 1

MeO PEG (750) cap (456)

A mixture of MeO PEG (750) (80 parts; 0.107M ex Fluka), ε-caprolactone (48.68 parts; 0.43M, ex Interox) and tetrabutyl titanate (0.4 parts; ex Aldrich) were stirred together under nitrogen for 6 hours at 160–180° C. The product (110 parts) was obtained as a light brown oil which formed a soft wax on cooling.

Intermediate 2

MeO PEG (750) cap (228)

Intermediate 2 was prepared by the same method as that described for Intermediate 1 above except that half the charge of ε-caprolactone was used. The product (100 parts) was obtained as a light brown oil.

Intermediate 3

MeO PEG (750) cap (798)

This was prepared in a analogous manner to Intermediate 1 except using MeO PEG (750) (50 parts; 0.066M) and ε-caprolactone (53.25 parts, 0.467M) in place of the quantities described in Intermediate 1. The product (100 parts) was obtained as a brown viscous oil which formed a waxy solid on cooling.

Intermediate 4

MeO PEG (750) cap (1026)

A mixture of MeO PEG (750) (40 parts; 0.053M) and ε-caprolactone (54.72 parts, 0.480M) were stirred together at 100° C. under nitrogen. Tetrabutyl titanate (0.4 parts) was added and the reactants stirred under nitrogen for 6 hours at 170–180° C. the product (90 parts) was obtained as a pale brown oil which formed a hard wax on cooling.

Intermediate 5

MeO PEG (750) γ-valerolactone (750)

A mixture of MeO PEG (750) (40 parts; 0.053 m) and γ-valerolactone (40 parts;

0.4M ex Aldrich) were heated to 150° C. Dibutyltindilaurate (0.5 parts ex Aldrich) was added and the reactants heated under nitrogen for 6 hours at 180–185° C. On cooling the product was obtained as a wax (75 parts).

Preparation of Phosphate ester Dispersants

Example 1

MeO PEG (750) cap (456) (1.5:1 with phosphorus)

Intermediate 1 (12.22 parts; 0.01M) was melted at 50° C. and charged to a reaction vessel under a nitrogen atmosphere. Phosphorus pentoxide (0.47 parts, 0.0033M) was added and the reactants stirred under nitrogen at 50° C. for 1 hour. The reaction was then continued for a further 16 hours under nitrogen at 80–90° C. This is Dispersant 1 and was obtained as a pale yellow oil which formed a soft waxy solid on cooling.

Example 2

MeO PEG (750) cap (228) (1.5:1 with phosphorus)

Dispersant 2 was prepared by the same method as that described in Example 1 above except that Intermediate 1 was replaced by the equivalent amount of Intermediate 2. Dispersant 2 was obtained as a pale yellow oil which solidified to a soft waxy solid on cooling.

Example 3

MeO PEG (750) cap (798) (1.5:1 with phosphorus)

This was prepared in analogous manner to that described for Example 1 except using Intermediate 3 (7.74 parts, 0.005 M) in place of Intermediate 1 and phosphorus pentoxide (0.24 parts; 0.0017 M). This is Dispersant 3 which was obtained as a pale yellow oil which formed a soft wax on cooling.

Example 4

MeO PEG (750) cap (1026) (1.5:1 with phosphorus)

This was prepared in analogous manner to that described in Example 1 except using Intermediate 4 (25.52 parts; 0.02M) in place of Intermediate 1 and also phosphorus pentoxide (0.95 parts; 0.0067 M). This is Dispersant 4 and was obtained as a yellow oil which formed a soft wax on cooling.

Example 5

MeO PEG (2000) cap (456) (1.5:1 with phosphorus)

MeO PEG (2000) (50 parts; 0.025M, ex Fluka), ε-caprolactone (11.41 parts, 0.1M, ex Interox) and tetrabutyltitanium (0.4 parts) were stirred together for 6 hours at 180–185° C. under a nitrogen atmosphere. The reactants were then cooled to 80° C. and polyphosphoric acid (2.78 parts) was added. The reactants were stirred for a further 24 hours at 90–950° C. under nitrogen. This is Dispersant 5 and was obtained as a pale coloured oil (60 parts) which formed a gel on cooling.

Example 6

MeO PEG (2000) cap (798) (1.5:1 with phosphorus)

This was prepared in identical manner to that described in Example 5 except that the amount of caprolactone was increased to 19.97 parts. This is Dispersant 6 and was obtained as a pale yellow viscous oil (65 parts) which formed a gel on cooling.

Example 7

MeO PEG (2000) cap (1026) 1.5:1 with phosphorus)

This was prepared in identical manner to that described in Example 5 except that the amount of caprolactone was increased to 25.67 parts. This is Dispersant 7 and was obtained as pale yellow oil (71 parts) which solidified to a waxy solid on cooling.

Example 8

MeO PEG (750) γ-valerolactone (750) (1.5:1 with phosphorus)

Intermediate 5 (40 parts) was heated with polyphosphoric acid (3.05 parts) at 95° C. for 4 hours under nitrogen. After cooling Dispersant 8 was obtained as a brown solid (40 parts).

Examples 9 to 11 and Comparative Examples A to D

Millbases were prepared with compositions as detailed in Table 1 by adding the dispersant to water and resin and adjusting the pH to about 10 by addition of ammonia followed by warming on a steam bath to ensure that the dispersant was fully dissolved. After cooling, the solution of dispersant was added to a dispermat pot and the titanium dioxide added whilst stirring. A quantity of 1 mm glass beads (180 parts) was added and the millbase milled at speed 3000 for 30 minutes without cooling water running through the cooling jacket. The millbase was then cooled and removed from the beads prior to adding to the letdown composition.

After standing for 16 hours at 15–20° C. to de-aerate, the paint was coated onto primed steel and aluminium panels using a No 8 K-bar fitted to an automatic coater (Model KCC 202) giving a 100 μ thick wet film. The film was air-dried for 90 minutes and then baked at 120° C. for 30 minutes. The 20° gloss for each panel was calculated from the mean of 5 readings taken over the panel surface. The results are given in Table 2.

Dispersants 3 and 4 failed to give a satisfactory millbase and were not letdown to give a final paint.

TABLE 1

| Dispersant | Ex. 9 | Ex. 10 | A | B | Ex. 11 | C | D |
|---|---|---|---|---|---|---|---|
| 1 | 4.8 | | | | | | |
| 2 | | 4.8 | | | | | |
| 3 | | | 4.8 | | | | |
| 4 | | | | 4.8 | | | |
| 8 | | | | | 4.8 | | |
| C | | | | | | 4.8 | |
| D | | | | | | | 4.8 |
| Water | 37.6 | 37.6 | 37.6 | 37.6 | 37.6 | 37.6 | 37.6 |
| AMP 95 | 0.6 | 0.6 | 0.6 | 0.6 | 0.6 | 0.6 | 0.6 |
| Tioxide TR 92 | 79.84 | 79.84 | 79.84 | 79.84 | 79.84 | 79.84 | 79.84 |
| Letdown | | | | | | | |
| Yield of paint | 60.1 | 36.1 | — | — | 65.88 | 80.09 | 53.29 |
| Neocryl XK 90 | 103.93 | 62.42 | — | — | 113.91 | 138.48 | 92.14 |
| Propylene glycol | 4.3 | 2.59 | — | — | 4.72 | 5.74 | 3.82 |

Footnote to Table 1

The paints were let down to final volume by adding Neocryl XK90 resin and propylene glycol in the amounts given by the formulae Weight of Neocryl resin=Y×212.4/122.8

Weight of propylene glycol=Y×8.8/122.8 where Y is the yield of paint.

AMP 95 is 2-amino-2-methyl-1-propanol available from Angus Chemie GmbH, Tioxide TR 92 is titanium diocide (ICI PLC) and Neocryl XK90 is an acrylic resin in a mixture of water and propylene glycol available from Zeneca Resins.

Dispersants 3 and 4 have a higher amount of polycaprolactone in the block copolymer relative to polyethyleneglycol monomethyl ether and failed to produce a satisfactory dispersion.

Dispersant C is MeO PEG (350) PHS (450) (1.5:1 with phosphorus) where PHS replaces the caprolactone and PHS is poly (12-hydroxystearic acid).

Dispersant D is MeO PEG (750) (1.5:1 with phosphorus) and has no caprolactone content.

TABLE 2

| | | Average 20° Gloss | |
|---|---|---|---|
| Example | Dispersant | Aluminium | Primed Steel |
| 9 | 1 | 45.68 | 38.28 |
| 10 | 2 | 41.86 | 35.22 |
| 11 | 8 | 43.32 | 36.68 |
| C | C | 36.40 | 38.52 |
| D | D | 35.88 | 31.62 |

Examples 12 to 14

Millbases were prepared having the compositions as detailed in Table 3 below by a similar method to that described in Examples 9 to 11. The resultant 20° gloss data is given in Table 4.

Millbases using Dispersants 5,6 and 7 gave very good dispersions which were free of solid bits.

TABLE 3

| Millbase | Example 12 | Example 13 | Example 14 |
|---|---|---|---|
| Dispersant 5 | 4.8 | | |
| Dispersant 6 | | 4.8 | |
| Dispersant 7 | | | 4.8 |
| Water | 37.6 | 37.6 | 37.6 |
| AMP 95 | 0.6 | 0.6 | 0.6 |
| Tioxide TR92 | 79.84 | 79.84 | 79.84 |
| Letdown | | | |
| Yield of Paint | 91.77 | 91 | 85.4 |
| Neocryl XK90 | 158.68 | 157.35 | 147.66 |
| Propylene glycol | 6.57 | 6.52 | 6.12 |

Footnote to Table 3

The letdown concentrations of Neocryl XK90 and propylene glycol were calculated described in the footnote to Table 1.

TABLE 4

| | | Average 20° Gloss | |
|---|---|---|---|
| Example | Dispersant | Aluminium | Primed Steel |
| 12 | 5 | 47.5 | 47.94 |
| 13 | 6 | 60.04 | 57.1 |
| 14 | 7 | 54.0 | 57.64 |

Examples 15–21

Millbases were prepared by adding dispersing agent (2.55 parts), Dehydran 1293 (0.3 part) and AMP 95 (0.23 parts) to a mixture of water (9.6 parts) and propylene glycol (6.75 parts). The pH was adjusted to about pH 10 and the mixture warmed to dissolve the components. The mixture was then cooled and poured into a dispermat pot. Neocryl XK90 (44.8 parts) and Tioxide TR 92 (64 parts) were added followed by 1 mm glass beads (180 parts). The millbase was then milled at speed 3000 for 30 minutes without external cooling. The millbase was then separated from the beads and let down to give the final paint formulation with further amounts of Neocryl XK90 as detailed in Table 5 below:

TABLE 5

| Example | Dispersant | Yield of paint | Amount of Neocryl XK90 in letdown |
|---|---|---|---|
| 15 | 1 | 32.74 | 33.96 |
| 16 | 2 | 43.50 | 45.12 |
| 17 | 4 | 16.23 | 16.84 |
| 18 | 5 | 48.40 | 50.20 |
| 19 | 6 | 60.0 | 62.23 |
| 20 | 7 | 66.66 | 69.14 |
| 21 | 8 | Nil | — |

Footnote to Table 5

The amount of Neocryl XK90 (X) in the letdown was calculated according to the formula Y×133.0/128.23 where Y is yield of paint.

Dehydran 1293 is an antifoam agent available from Henkel GmbH, AMP95 is 2amino-2-methyl-1-propanol, Neocryl XK90 is an acrylic resin in a mixture of water and propyleneglycol available from Zeneca Resins and Tioxide TR 90 is titanium dioxide available from ICI PLC.

When Dispersant 8 was used to prepare a millbase it failed to give a satisfactory dispersion when the milling was carried out in the presence of Neocryl XK90.

The above paints were allowed to stand for 16 hours to de-aerate and were then ted onto primed steel and aluminium panels using an automatic coater, model KCC 202, fitted with a No. 8 K-bar. The paint films were air-dried for 90 minutes and then cured by baking for 30 minutes at 120° C. The 2020 gloss of the final paint films were determined and the results given in Table 6 below:

TABLE 6

| | | 20° Gloss | |
|---|---|---|---|
| Example | Dispersant | Aluminium | Primed Steel |
| 15 | 1 | 53.32 | 50.27 |
| 16 | 2 | 52.13 | 43.88 |
| 17 | 4 | 48.02 | 46.54 |
| 18 | 5 | 55.70 | 51.00 |
| 19 | 6 | 54.32 | 49.68 |
| 20 | 7 | 56.74 | 51.92 |

What is claimed is:

1. A dispersant which is a phosphate ester of a block copolymer of formula 1

$$RO(C_2H_4O)_m (PES)_n\text{—H} \quad\quad 1$$

wherein

R is $C_{1-4}$-alkyl;

PES is a polyester derived from a cyclic lactone;

m is from 5 to 60;

n is from 2 to 30; and where the molecular weight of $RO(C_2H_4O)_m$ is greater than the molecular weight of $(PES)_n$.

2. A dispersant as claimed in claim 1 wherein R is methyl.

3. A dispersant as claimed in either claim 1 or claim 2 wherein PES represents a polyester derived from ε-caprolactone.

4. A dispersant as claimed in any one of claims 1 to 3 wherein the ratio of m:n is not less than 3:1.

5. A dispersant as claimed in any one of claims 1 to 4 which is a mixture of mono-and di-phosphate.

6. A composition comprising a dispersant as claimed in any one of claims 1 to 5 and a particulate solid.

7. A composition as claimed in claim 6 which additionally comprises a liquid medium.

8. A composition as claimed in claim 7 wherein the liquid medium is water.

9. An aqueous millbase comprising a dispersant as claimed in any one of claims 1 to 5, a particulate solid and a film-forming resin.

10. A paint or ink comprising a dispersant as claimed in any one of claims 1 to 5, a particulate solid and a film-forming resin.

* * * * *